United States Patent [19]

Hamamura et al.

[11] Patent Number: 5,412,124
[45] Date of Patent: May 2, 1995

[54] PREPARATION PROCESS OF NAPHTHOQUINONE DERIVATIVE AND INTERMEDIATE FOR THE PREPARATION THEREOF

[75] Inventors: Kimio Hamamura, Chiba; Chiaki Seki, Aichi; Masayuki Konishi, Ibaraki, all of Japan

[73] Assignee: Eisai Chemical Co., Ltd., Ibaraki, Japan

[21] Appl. No.: 280,550

[22] Filed: Jul. 26, 1994

[30] Foreign Application Priority Data

Jul. 26, 1993 [JP] Japan .................................. 5-202551
Dec. 15, 1993 [JP] Japan .................................. 5-342215

[51] Int. Cl.[6] ............................................ C07C 50/00
[52] U.S. Cl. .................................................. 552/299
[58] Field of Search ...................................... 552/299

[56] References Cited

U.S. PATENT DOCUMENTS 4,374,775 2/1982 Dötz ..................... 552/299
4,853,156 8/1989 Rüttiman et al. .......... 552/299

*Primary Examiner*—Howard T. Mars
*Assistant Examiner*—Rebecca Cook
*Attorney, Agent, or Firm*—Wenderoth, Lind & Ponack

[57] ABSTRACT

Disclosed herein are a naphthoquinone derivative represented by the following formula:

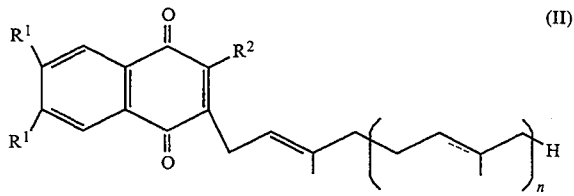

wherein $R^1$ means a hydrogen atom or methyl group, $R^2$ is a hydrogen atom or methyl group, n stands for 0 or an integer of 1–9, and a linkage ⚌ is a single bond or double bond with the proviso that if n is an integer of 2–9, the linkages may be identical with or different optionally from each other, such as a vitamin K derivative; and a process for producing the naphthoquinone derivative at a high yield without forming any geometric isomer; as well as 1,4,4$_a$,5,8,9$_a$-hexahydro-4$_a$α-alkenyl-1α,4α-methanoanthraquinone derivatives and 1,4,4$_a$,5,8,9$_a$-hexahydro-1α,4α-methanoanthraquinone derivatives which are useful as intermediates for the preparation of the naphthoquinone derivatives.

7 Claims, No Drawings

PREPARATION PROCESS OF NAPHTHOQUINONE DERIVATIVE AND INTERMEDIATE FOR THE PREPARATION THEREOF

BACKGROUND OF THE INVENTION

1. Field of the Invention

The present invention relates to new industrial processes for the preparation of vitamin K derivatives, which play an important role in the vital body as hematostatic vitamins, and intermediates useful for the preparation thereof.

2. Description of the Background Art

Naphthoquinone derivatives, which are vitamin K derivatives, have heretofore been prepared by reacting 2-methyl-1,4-naphthoquinone (menadione) or the like with an allyl halide derivative by the Friedel-Crafts reaction.

Besides, Japanese Patent Application Laid-Open (KOKAI) No. 56935/1985 discloses a process for preparing a naphthoquinone derivative by forming 1,4,4$_a$α,9$_a$-tetrahydro-9$_a$α-methyl-1α,4α-methanoanthraquinone from 2-methyl-1,4-naphthoquinone and cyclopentadiene, reacting this product with an allyl halide derivative into a 1,4,4$_a$α,9$_a$-tetrahydro-9$_a$α-methyl-4α-alkenyl-1α,4α-methanoanthraquinone, and then refluxing the thus-obtained product under heat in a toluene solvent to conduct a Retro Dieis-Alder reaction. In the conventional processes for preparing naphthoquinone derivatives, 2-methyl-1,4-naphthoquinone which is a starting material has been extremely expensive and hence difficult to obtain in a great amount on an industrial scale. Further, naphthoquinone derivatives produced by conducting the Friedel-Crafts reaction undergo geometric isomerization on the allyl group as indicated by the following chemical reaction formula. Therefore, the final product is provided as a mixture of an intended trans (E) isomer and a cis (Z) isomer formed as a by-product. In addition, they are very difficult to separate from each other to purify them because their physicochemical properties are similar to each other. Accordingly, this process has not been said to be an industrially or economically satisfactory process.

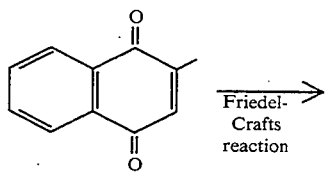

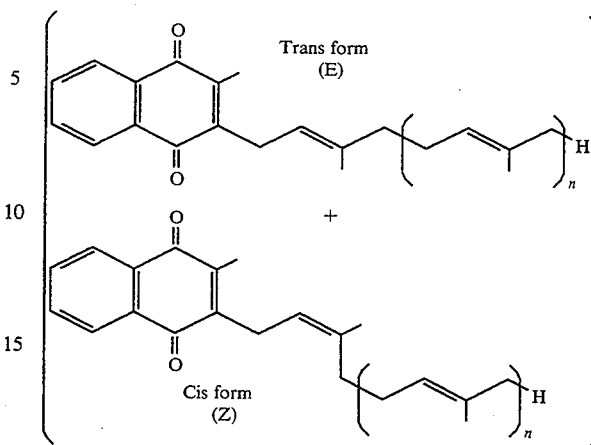

On the other hand, the process disclosed in Japanese Patent Application Laid-Open (KOKAI) No. 56935/1985 can improve the disadvantage that the geometric isomers are formed, but has remained using 2-methyl-1,4-naphthoquinone as a starting material. Therefore, a problem has remained unsolved from the viewpoint of obtaining the starting material.

In addition, the process disclosed in Japanese Patent Application Laid-Open (KOKAI) No. 56935/1985 requires a strong base such as a metal amide, lithium dialkylamide, alkali metal t-butyrate, sodium hydride or potassium hydride for the reaction of 1,4,4$_a$α,9$_a$-tetrahydro-9$_a$α-methyl-1α,4α-methanoanthraquinone or the like with an allyl halide derivative. However, these strong bases are materials difficult to industrially handle in a great amount from the viewpoint of flammability, corrosiveness, decomposition behavior due to moisture absorption, toxicity, shelf stability and the like. This process has not been said to be always an industrially suitable process.

1,4,4$_a$α,9$_a$-Tetrahydro-9$_a$α-methyl-1,α,4α-methanoanthraquinone or the like, which is a starting material in the above publication, is obtained by the Dieis-Alder reaction of 2-methyl-1,4-naphthoquinone, 2,3-dimethoxy-5-methylbenzoquinone or the like with cyclopentadiene. However, this addition reaction is extremely slow, and it takes four long days to complete the reaction as described in Examples of the above publication. Such a process has hence been disadvantageous from the industrial viewpoint.

As described above, the disadvantage of forming the geometric isomers, the problem from the viewpoint of obtaining starting materials, the difficulty of handling the bases, or the time problem involved in the preparation of the starting material has not been yet solved in the conventionally-known processes. Therefore, such processes all have been insufficient for industrial processes. With such a background, there has been demand for development of an industrially excellent preparation process for naphthoquinone derivatives, by which an intended naphthoquinone derivative can be prepared from cheap and easily available starting materials with good operating simplicity for a short period of time without forming any geometric isomer.

SUMMARY OF THE INVENTION

Therefore, the present inventors have carried out an extensive investigation with a view toward improving the above-described problems involved in the conventionally-known processes. As a result, it has been found that when a 5,8-dihydro-1,4-naphthoquinone (V) derived from a cheap and easily available 1,4-benzoquinone, methyl-1,4-benzoquinone (p-toluquinone) or the like is used to react it with cyclopentadiene into a 1,4,4$_a$,5,8,9$_a$-hexahydro-1α,4α-methanoanthraquinone derivative (III) in accordance with the Dieis-Alder reaction, the derivative (III) is reacted with an allyl derivative (IV) in the presence of a base into a 1,4,4$_a$,5,8,9$_a$-hexahydro-4$_a$α-alkenyl-1α,4α-methanoanthraquinone derivative (I), and the derivative (I) is then subjected to a Retro Dieis-Alder reaction in the presence of a dehydrogenating agent or oxidizing agent, a naphthoquinone derivative (II) can be industrially prepared with ease at a high yield without forming any geometric isomer while attaining the desired ends, thus leading to completion of the present invention. The outline of the reaction paths in the present invention is shown by the following chemical reaction formula:

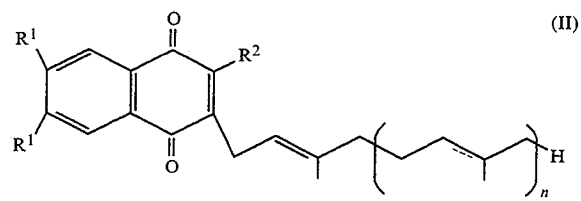

wherein R$^1$, R2, n and a linkage ⚌ have the same meaning as defined above, which comprises subjecting a 1,4,4$_a$,5,8,9$_a$-hexahydro-4$_a$α-alkenyl-1α,4α-methanoanthraquinone derivative represented by the following formula (I):

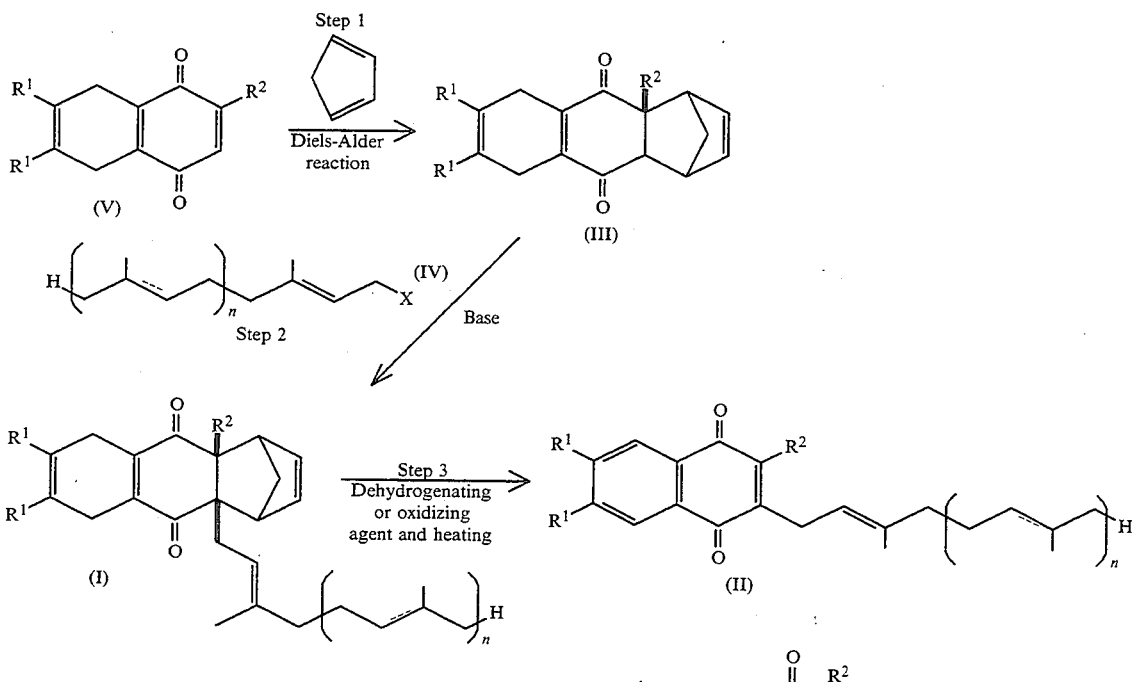

wherein R$^1$ means a hydrogen atom or methyl group, R$^2$ is a hydrogen atom or methyl group, n stands for 0 or an integer of 1–9, and a linkage is a single bond (>CH—CH<) or a double bond (>C=C<) with the proviso that if n is an integer of 2–9, the linkages may be identical with or different optionally from each other.

It is therefore an object of the present invention to provide an industrially excellent process for preparing vitamin K derivatives, which play an important role in the vital body as hematostatic vitamins, and intermediates useful for the preparation thereof.

In an aspect of the present invention, there is thus provided a process for the preparation of a naphthoquinone derivative represented by the following formula (II):

wherein R$^1$, R2, n and a linkage ⚌ have the same meaning as defined above, to a Retro Dieis-Alder reaction in the presence of a dehydrogenating agent or oxidizing agent.

In another aspect of the present invention, there is also provided a process for the preparation of a naphthoquinone derivative represented by the formula (II), which comprises reacting a 1,4,4$_a$,5,8,9$_a$-hexahydro-1α,4α-methanoanthraquinone derivative represented by the following formula (III):

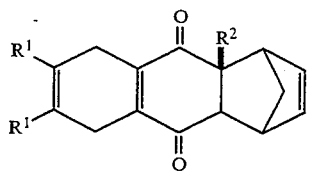

(III)

wherein R¹ and R² have the same meaning as defined above, with an allyl derivative represented by the following formula (IV):

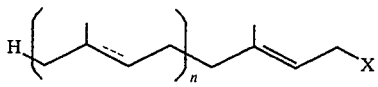

(IV)

wherein n and a linkage ╌ have the same meaning as defined above, and X means a halogen atom, alkylsulfonyl group or arylsulfonyl group, in the presence of a base to form a 1,4,4$_a$,5,8,9$_a$-hexahydro-4$_a$α-alkenyl-1α,4α-methanoanthraquinone derivative represented by the formula (I), and then subjecting the thus-formed derivative (I) to a Retro Dieis-Alder reaction in the presence of a dehydrogenating agent or oxidizing agent.

In a further aspect of the present invention, there is provided a process for the preparation of a naphthoquinone derivative represented by the formula (II), which comprises subjecting a 5,8-dihydro-1,4-naphthoquinone derivative represented by the following formula (V):

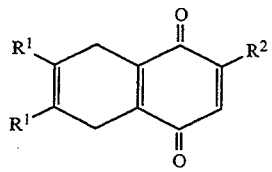

(V)

wherein R¹ and R² have the same meaning as defined above, and cyclopentadiene to a Dieis-Alder reaction into a 1,4,4$_a$,5,8,9$_a$-hexahydro-1α,4α-methanoanthraquinone derivative represented by the formula (III), reacting the derivative (III) with an allyl derivative represented by the formula (IV) in the presence of a base to form a 1,4,4$_a$,5,8,9$_a$-hexahydro-4$_a$α-alkenyl-1α,4α-methanoanthraquinone derivative represented by the formula (I), and subjecting the thus-formed derivative (I) to a Retro Dieis-Alder reaction in the presence of a dehydrogenating agent or oxidizing agent.

In a still further aspect of the present invention, there is provided a 1,4,4$_a$,5,8,9$_a$-hexahydro-4$_a$α-alkenyl-1α,-4α-methanoanthraquinone derivative represented by the formula (I).

In a yet still further aspect of the present invention, there is provided a 1,4,4$_a$,5,8,9$_a$-hexahydro-1α,4α-methanoanthraquinone derivative represented by the formula (III).

The above and other objects, features and advantages of the present invention will become apparent from the following description and the appended claims.

DETAILED DESCRIPTION OF THE INVENTION AND PREFERRED EMBODIMENTS

The 1,4,4$_a$,5,8,9$_a$-hexahydro-4$_a$α-alkenyl-1α,4α-methanoanthraquinone derivatives useful in the practice of the present invention are represented by the following formula (I):

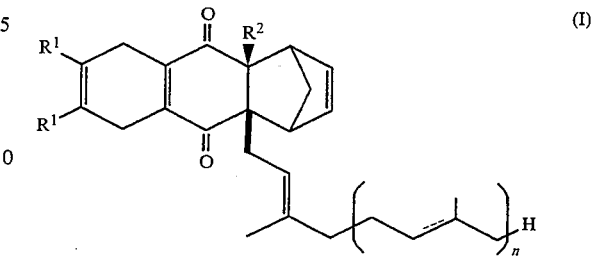

(I)

In the formula (I), R¹ means a hydrogen atom or methyl group, R² is a hydrogen atom or methyl group n , stands for 0 or an integer of 1–9, and a linkage ╌ is a single bond (>CH—CH<) or a double bond (>C═C<) with the proviso that if n is an integer of 2–9, the linkages may be identical with or different optionally from each other. Specific examples of the 1,4,4$_a$,5,8,9$_a$-hexahydro-4$_a$α-alkenyl-1α,4α-methanoanthraquinone derivatives (I) may include the following compounds though they are not limited to such compounds in the present invention.

(1) 1,4,4$_a$,5,8,9$_a$-Hexahydro-4$_a$α-(3'-methyl-2'-butenyl)-1α,4α-methanoanthraquinone;

(2) 1,4,4$_a$,5,8,9$_a$-Hexahydro-9$_a$α-methyl-4$_a$α-(3'-methyl-2'-butenyl) -1α,4α-methanoanthraquinone;

(3) 1,4,4$_a$,5,8,9$_a$-Hexahydro-7,8-dimethyl-4$_a$α-(3'-methyl-2'-butenyl) -1α,4α-methanoanthraquinone;

(4) 1,4,4$_a$,5,8,9$_a$-Hexahydro-7,8,9$_a$α-trimethyl-4$_a$α-(3'-methyl-2'-butenyl) -1α,4α-methanoanthraquinone;

(5) 1,4,4$_a$,5,8,9$_a$-Hexahydro-4$_a$α-(3',7'-dimethyl-2',6'-octadienyl)-1α,4 α-methanoanthraquinone;

(6) 1,4,4$_a$,5,8,9$_a$-Hexahydro-9$_a$α-methyl-4$_a$α-(3',7'-dimethyl-2',6'-octadienyl)-1α,4α-methanoanthraquinone;

(7) 1,4,4$_a$,5,8,9$_a$-Hexahydro-7,8-dimethyl-4$_a$α-(3',7'-dimethyl-2',6'-octadienyl)-1α,4α-methanoanthraquinone;

(8) 1,4,4$_a$,5,8,9$_a$-Hexahydro-7,8,9$_a$α-trimethyl-4$_a$α-(3',7'-dimethyl-2',6'-octadienyl)-1α,4α-methanoanthraquinone;

(9) 1,4,4$_a$,5,8,9$_a$-Hexahydro-4$_a$α-(3',7',11'-trimethyl-2',6',10'-dodecatrienyl)-1α,4α-methanoanthraquinone;

(10) 1,4,4$_a$,5,8,9$_a$-Hexahydro-9$_a$α-methyl-4$_a$α-(3',7',11'-trimethyl-2', 6',10'-dodecatrienyl)-1α,4α-methanoanthraquinone;

(11) 1,4,4$_a$,5,8,9$_a$-Hexahydro-7,8-dimethyl-4$_a$α-(3',7',11'-trimethyl-2',6', 10'-dodecatrienyl)-1α,4α-methanoanthraquinone;

(12) 1,4,4$_a$,5,8,9$_a$-Hexahydro-7,8,9$_a$α-trimethyl-4$_a$α-(3',7',11'-trimethyl -2',6',10'-dodecatrienyl)-1α,4α-methano-anthraquinone;

(13) 1,4,4$_a$,5,8,9$_a$-Hexahydro-4$_a$α-(3',7',11',15'-tetramethyl-2',6',10', 14,'-hexadecatetraenyl)-1α,4α-methanoanthraquinone;

(14) 1,4,4$_a$,5,8,9$_a$-Hexahydro-9$_a$α-methyl-4$_a$α-(3',7',11',15'-tetramethyl -2',6',10',14'-hexadecatetraenyl)-1α,4α-methanoanthraquinone;

(15) 1,4,4$_a$,5,8,9$_a$-Hexahydro-7,8-dimethyl-4$_a$α-(3',7',11',15'-tetramethyl -2',6',10',14'-hexadecatetraenyl)-1α,4α-methanoanthraquinone;

(16) 1,4,4$_a$,5,8,9$_a$-Hexahydro-7,8,9$_a$α-trimethyl-4$_a$α-(3',7',11',15'-tetramethyl-2',6',10',14'-hexadecatetraenyl)-1α,4α-methanoanthraquinone;

(17) 1,4,4$_a$,5,8,9$_a$-Hexahydro-4$_a$α-(3',7',11',15',19'-pentamethyl-2',6', 10',14',18'-eicosadecaheptaenyl)-1α,4α-methanoanthraquinone;

(18) 1,4,4$_a$,5,8,9$_a$-Hexahydro-9$_a$α-methyl-4$_a$α-(3',7',11',15',19'-pentamethyl-2',6',10',14',18'-eicosadecaheptaenyl)-1α,4α-methanoanthraquinone;

(19) 1,4,4$_a$,5,8,9$_a$-Hexahydro-7,8-dimethyl-4$_a$α-(3',7',11',15',19'-pentamethyl-2',6',10',14',18'-eicosadecaheptaenyl)-1α,4α-methanoanthraquinone;

(20) 1,4,4$_a$,5,8,9$_a$-Hexahydro-7,8,9$_a$α-trimethyl-4$_a$α-(3',7',11',15',19'-pentamethyl-2',6',10',14',18'-eicosadecaheptaenyl)-1α,4α-methanoanthraquinone;

(21) 1,4,4$_a$,5,8,9$_a$-Hexahydro-4$_a$α-(3',7', 11',15'-tetramethyl-2'-hexadecaenyl)-1α,4α-methanoanthraquinone;

(22) 1,4,4$_a$,5,8,9$_a$-Hexahydro-9$_a$α-methyl-4$_a$α-(3',7',11',15'-tetramethyl-2'-hexadecaenyl)-1α,4α-methanoanthraquinone;

(23) 1,4,4$_a$,5,8,9$_a$-Hexahydro-7,8-dimethyl-4$_a$α-(3',7',11',15'-tetramethyl -2'-hexadecaenyl)-1α,4α-methanoanthraquinone; and

(24) 1,4,4$_a$,5,8,9$_a$-Hexahydro-7,8,9$_a$α-trimethyl-4$_a$α-(3',7',11',15'-tetramethyl-2'-hexadecaenyl)-1α,4α-methanoanthraquinone.

The naphthoquinone derivatives according to the present invention are represented by the following formula (II):

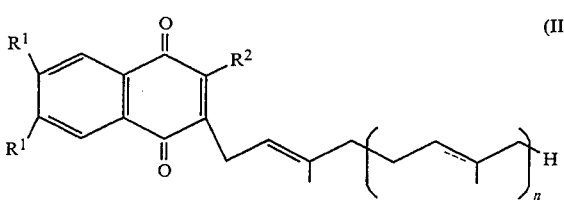

In the formula (II), $R^1$, $R^2$, n and a linkage ⩬ have the same meaning as defined above. Specific examples of the naphthoquinone derivatives (II) may include the following compounds though they are not limited to such compounds in the present invention.

(1) 2-(3'-Methyl-2'-butenyl)-1,4-naphthoquinone;
(2) 2-Methyl-3-(3'-methyl-2'-butenyl)-1,4-naphthoquinone;
(3) 6,7-Dimethyl-(3'-methyl-2'-butenyl)-1,4-naphthoquinone;
(4) 2,6,7-Trimethyl-3-(3'-methyl-2'-butenyl)-1,4-naphthoquinone;
(5) 2-(3',7'-Dimethyl-2',6'-octadienyl)-1,4-naphthoquinone;
(6) 2-Methyl-3-(3',7'-dimethyl-2',6'-octadienyl)-1,4-naphthoquinone;
(7) 6,7-Dimethyl-4$_a$α-(3',7'-dimethyl-2',6'-octadienyl)-1,4-naphthoquinone;
(8) 2,6,7-Trimethyl-3-(3',7'-dimethyl-2',6'-octadienyl)-1,4-naphthoquinone;
(9) 2-(3',7',11'-Trimethyl-2',6',10'-dodecatrienyl)-1,4-naphthoquinone;
(10) 2-Methyl-3-(3',7',11'-trimethyl-2',6',10'-dodecatrienyl)-1,4-naphthoquinone;

(11) 6,7-Dimethyl-2-(3',7',11'-trimethyl-2',6',10'-dodecatrienyl)-1,4-naphthoquinone;
(12) 2,6,7-Trimethyl-4$_a$α-(3',7',11'-trimethyl-2',6',10'--dodecatrienyl)-1,4-naphthoquinone;
(13) 2-(3',7',11',15'-Tetramethyl-2',6',10',14'-hexadecatetraenyl)-1,4-naphthoquinone;
(14) 2-Methyl-3-(3',7',11',15'-tetramethyl-2',6',10',14'--hexadecatetraenyl) -1,4-naphthoquinone;
(15) 6,7-Dimethyl-2-(3',7',11',15'-tetramethyl-2',6',10',14'-hexadecatetraenyl) -1,4-naphthoquinone;
(16) 2,6,7-Trimethyl-3-(3',7',11',15'-tetramethyl-2',6',1-0',14'--hexadecatetraenyl) -1,4-naphthoquinone;
(17) 2-(3',7',11',15',19'-Pentamethyl-2',6',10',14',18'-eicosadecaheptaenyl) -1,4-naphthoquinone;
(18) 2-Methyl-3-(3',7',11',15',19'-pentamethyl-2',6',10',14',18'-eicosadecaheptaenyl)-1,4-naphthoquinone;
(19) 6,7-Dimethyl-2-(3',7',11',15',19'-pentamethyl-2',6',10',14',18' -eicosadecaheptaenyl)-1,4-naphthoquinone;
(20) 2,6,7-Trimethyl-3-(3',7',11',15',19'-pentamethyl-2',6',10',14',18'-eicosadecaheptaenyl)-1,4naphthoquinone;
(21) 2-(3',7',11',15'-Tetramethyl-2'-hexadecaenyl)-1,4-naphthoquinone;
(22) 2-Methyl-3-(3',7',11',15'-tetramethyl-2'-hexadecaenyl)-1,4-naphthoquinone;
(23) 6,7-Dimethyl-4$_a$α-(3',7',11',15'-tetramethyl-2'-hexadecaenyl)-1,4-naphthoquinone; and
(24) 2,6,7-Trimethyl-3-(3',7',11',15'-tetramethyl-2'-hexadecaenyl)-1,4-naphthoquinone.

The 1,4,4$_a$,5,8,9$_a$-hexahydro-1α,4α-methanoanthraquinone derivatives useful in the practice of the present invention are represented by the following formula (III):

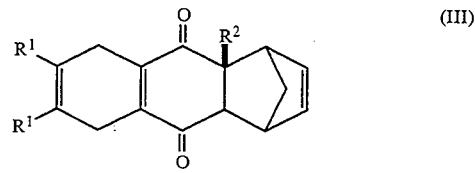

In the formula (III), $R^1$ and $R^2$ have the same meaning as defined above. Specific examples of the 1,4,4$_a$,5,8,9$_a$-hexahydro-1α,4α-methanoanthraquinone derivatives (III) may include the following compounds though they are not limited to such compounds in the present invention.

(1) 1,4,4$_a$,5,8,9$_a$-Hexahydro-1α,4α-methanoanthraquinone;
(2) 1,4,4$_a$,5,8,9$_a$-Hexahydro-9$_a$α-methyl-1α,4α-methanoanthraquinone;
(3) 1,4,4$_a$,5,8,9$_a$-Hexahydro-7,8-dimethyl-1α,4α-methanoanthraquinone; and
(4) 1,4,4$_a$,5,8,9$_a$-Hexahydro-7,8,9$_a$α-trimethyl-1α,4α-methanoanthraquinone.

The allyl derivatives useful in the practice of the present invention are represented by the following formula (IV):

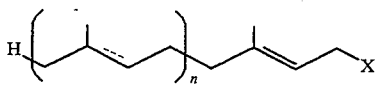

(IV)

In the formula (IV), X means a halogen atom, alkylsulfonyl group or arylsulfonyl group. Specific examples of the halogen atom may include bromine, iodine, chlorine and fluorine atoms. Specific examples of the alkylsulfonyl group may include sulfonyl groups having a $c_{1-6}$ alkyl group in its molecule, such as methanesulfonyl and ethanesulfonyl groups. Specific examples of the arylsulfonyl group may include sulfonyl groups having a unsubstituted or substituted aryl group in its molecule, such as benzenesulfonyl and toluenesulfonyl groups. n stands for 0 or an integer of 1–9, and a linkage ≔ has the same meaning as defined above.

Incidentally, various geometric isomers (E-Z isomers or cis-trans isomers) exist in the allyl derivatives (IV). However, no limitation is imposed on such compounds, and any isomers may hence be used in the present invention. Specific examples of the allyl derivatives (IV) may include the following compounds though they are not limited to such compounds in the present invention.

(1) 3'-Methyl-2'-butenyl bromide;
(2) 3'-Methyl-2'-butenyl chloride;
(3) 3'-Methyl-2'-butenyl iodide;
(4) 3'-Methyl-2'-butenyl methanesulfonate;
(5) 3'-Methyl-2'-butenyl ethanesulfonate;
(6) 3'-Methyl-2'-butenyl benzenesulfonate;
(7) 3'-Methyl-2'-butenyl p-toluenesulfonate;
(8) Geranyl bromide;
(9) Farnesyl bromide;
(10) Geranylgeranyl bromide;
(11) Geranylfarnesyl bromide;
(12) Farnesylfarnesyl bromide;
(13) Solanesyl bromide; and
(14) Phytyl bromide.

The 5,8-dihydro-1,4-naphthoquinone derivatives useful in the practice of the present invention are represented by the following formula (V):

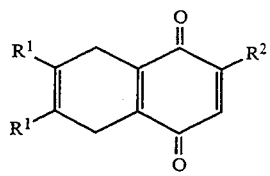

(V)

In the formula (V), $R^1$ and $R^2$ have the same meaning as defined above. Specific examples of the 5,8-dihydro-1,4-naphthoquinone derivatives (V) may include the following compounds though they are not limited to such compounds in the present invention.

(1) 5,8-Dihydro-1,4-naphthoquinone;
(2) 5,8-Dihydro-2-methyl-1,4-naphthoquinone;
(3) 5,8-Dihydro-6,7-dimethyl-1,4-naphthoquinone; and
(4) 5,8-Dihydro-2,6,7-trimethyl-1,4-naphthoquinone.

Incidentally, the 5,8-dihydro-1,4-naphthoquinone derivative (V) is a starting material in the present invention and may be prepared in accordance with the process described in Journal of The Chemical Society of Japan, 63(10), 1354–1360 (1942), or Japanese Patent Application Laid-Open (KOKAI) No. 134581/1982.

The 1,4,4$_a$,5,8,9$_a$-hexahydro-4$_a$α-alkenyl-1α,4α-methanoanthraquinone derivatives (I) and 1,4,4$_a$,5,8,9$_a$-hexahydro-1α,4α-methanoanthraquinone derivatives (III) useful in the practice of the present invention are novel compounds and useful as intermediates for the preparation of the naphthoquinone derivatives (II). Specific examples of these compounds may include the above-mentioned compounds.

The individual steps in the preparation processes according to the present invention will hereinafter be described in detail (see the chemical reaction formula shown on page 5).

STEP 1

This step is a process in which cyclopentadiene is added to a 5,8-dihydro-1,4-naphthoquinone derivative (V) by the Diels-Alder reaction to prepare a 1,4,4$_a$,5,8-,9$_a$-hexahydro-1α,4α-methanoanthraquinone derivative (III). In general, this addition can be performed in accordance with the usual Diels-Alder reaction. In the present invention, however, the derivative (III) can be prepared by adding fresh cyclopentadiene as distilled at room temperature to the 5,8-dihydro-1,4-naphthoquinone derivative (V) which may or may not be dissolved in a solvent. When a Lewis acid, scandium trifluoromethanesulfonate, lanthanium trifluoromethanesulfonate, ytterbium trifluoromethanesulfonate or the like is added as a catalyst, it is also possible to accelerate the reaction and improve the yield and purity of the intended product.

In the case where the solvent is used, no limitation is imposed on the solvent to be used so long as it is inert on the 5,8-dihydro-1,4-naphthoquinone derivative (V) or cyclopentadiene. Specific examples thereof may include methanol, ethanol, n-propanol, i-propanol, n-butanol, i-butanol, t-butanol, formic acid, acetic acid, propionic acid, butyric acid, methylene chloride, chloroform, carbon tetrachloride, trichlene, nitromethane, tetrahydrofuran, 1,2-dimethoxyethane, ethyl ether, isopropyl ether, methyl acetate, ethyl acetate, propyl acetate, methyl propionate, ethyl propionate, methyl butyrate, ethyl butyrate, acetone, 2-butanone, 1,4-dioxane, 1,3-dioxolan, N,N-dimethylformamide, dimethylsulfoxide, hexamethylphosphoric triamide (HMPA), hexamethylphosphorous triamide (HMPT), benzene, toluene, xylene, nitrobenzene, etc., with methanol, ethanol, n-propanol, i-propanol, n-butanol, i-butanol, t-butanol, formic acid, acetic acid and propionic acid being more preferred.

No limitation is imposed on the amount of the solvent to be used. However, it is generally used in an amount of about 0.5–100 parts by volume, preferably about 0.5–50 parts by volume, more preferably about 1–20 parts by volume per part by weight of the 5,8-dihydro-1,4-naphthoquinone derivative (V). Incidentally, the solvents may be used either singly or in any combination thereof.

Further, no limitation is imposed on the amount of cyclopentadiene to be used in the present invention. However, it is generally used in an amount of about 1–10 equivalents, preferably about 1–7 equivalents, more preferably about 1–5 equivalents based on the 5,8-dihydro-1,4-naphthoquinone derivative (V).

If the catalyst is used, no limitation is imposed on the amount of the catalyst to be used. In the case where the Lewis acid is used, however, it is generally used in an amount of about 0.7–10.0 equivalents, preferably about 0.8–5.0 equivalents, more preferably about 0.9–2.0 equivalents based on the 5,8-dihydro-1,4-naphthoquinone derivative (V). On the other hand, in the case where scandium trifluoromethanesulfonate, lanthanium trifluoromethane-sulfonate, ytterbium trifluoromethanesulfonate or the like is used, it is generally used in an amount of about 0.00001–5.0 equivalents, preferably about 0.0001–3.0 equivalents, more preferably about 0.001–1.0 equivalent based on the 5,8-dihydro-1,4-naphthoquinone derivative (V). These catalysts may be used either singly or in any combination thereof.

The reaction in this step may be conducted in a temperature range of from −40° C. to a reflux temperature of the solvent, generally, at room temperature. The reaction is generally completed in about 6–72 hours.

Incidentally, the crude 1,4,4$_a$,5,8,9$_a$-hexahydro-1α,4α-methanoanthraquinone derivative (III) formed can be purified by the conventionally-known method such as recrystallization, column chromatography on silica gel or HPLC.

STEP 2

This step is a process in which an allyl derivative (IV) is added to the 1,4,4$_a$,5,8,9$_a$-hexahydro-1α,4α-methanoanthraquinone derivative (III) obtained in the preceding step in the presence of a base to prepare a 1,4,4$_a$,5,8,9$_a$-hexahydro-4$_a$α-alkenyl-1α,4α-methanoanthraquinone derivative (I). This process may be generally carried out in accordance with the conventionally-known method for the C-alkylation of a methylene or methine group situated at an α position of a ketone. In the present invention, however, the derivative (I) can be prepared either by dissolving or suspending a base in a solvent, adding the 1,4,4$_a$,5,8,9$_a$-hexahydro-1α,4α-methanoanthraquinone derivative (III) thereto and then adding the allyl derivative (IV), or by dissolving the 1,4,4$_a$,5,8,9$_a$-hexahydro-1α,4α-methanoanthraquinone derivative (III) in a solvent, adding the base thereto and then adding the allyl derivative (V). In this step, the reaction may preferably be conducted in an inert gas stream. However, no limitation is imposed on this process, and it may hence be performed in no inert gas stream.

When the allyl derivative (V) is added to the 1,4,4$_a$,5,8,9$_a$-hexahydro-1α,4α-methanoanthraquinone derivative (III), the reaction is conducted in the presence of the base. Specific examples of the base may include sodium methoxide, sodium ethoxide, potassium methoxide, potassium ethoxide, potassium t-butoxide, sodium hydride, potassium hydride, calcium hydride, lithium hydride, n-butyllithium, sodium amide, lithium amide, lithium dimethylamide, lithium diethylamide, lithium diisopropylamide, lithium dicyclohexylamide, metallic sodium, metallic potassium, metallic lithium, sodium hydroxide, potassium hydroxide, sodium carbonate, potassium carbonate, etc.

No limitation is imposed on the amount of the base to be used. However, it is generally used in an amount of about 0.8–10 equivalents, preferably about 0.9–7 equivalents, more preferably about 1.0–5 equivalents based on the 1,4,4$_a$,5,8,9$_a$-hexahydro-1α,4α-methanoanthraquinone derivative (III).

No limitation is also imposed on the amount of the allyl derivative (V) to be used. However, it is generally used in an amount of about 0.8–10 equivalents, preferably about 0.9–5 equivalents, more preferably about 1.0–3 equivalents based on the 1,4,4$_a$,5,8,9$_a$-hexahydro-1α,4α-methanoanthraquinone derivative (III).

Further, no limitation is imposed on the solvents to be used in this step so long as they are inert on the base, 1,4,4$_a$,5,8,9$_a$-hexahydro-1α,4α-methanoanthraquinone derivative (III) or allyl derivative (IV). Specific examples thereof may include tetrahydrofuran, 1,2-dimethoxyethane, 2-methoxyethyl ether, ethyl ether, isopropyl ether, methyl acetate, ethyl acetate, propyl acetate, methyl propionate, ethyl propionate, methyl butyrate, ethyl butyrate, N,N-dimethylformamide, dimethylsulfoxide, 1,4-dioxane, 1,3-dioxolan, hexamethylphosphoric triamide (HMPA), hexamethyl-phosphorous triamide (HMPT), benzene, toluene, xylene, nhexane, pentane, octane, petroleum ether, etc. Of these, tetrahydrofuran, 1,2-dimethoxyethane, 2-methoxyethyl ether, ethyl ether, N,N-dimethylformamide, dimethylsulfoxide, hexamethylphosphoric triamide, hexamethyl-phosphorous triamide, toluene and n-hexane are preferred, with tetrahydrofuran, 1,2-dimethoxyethane, 2-methoxyethyl ether and n-hexane being more preferred.

No limitation is imposed on the amount of the solvent to be used. However, it is generally used in an amount of about 0.5–100 parts by volume, preferably about 0.5–50 parts by volume, more preferably about 1–20 parts by volume per part by weight of the 1,4,4$_a$,5,8,9$_a$-hexahydro-1α,4α-methanoanthraquinone derivative (III). Incidentally, the solvents may be used either singly or in any combination thereof.

The reaction in this step may be conducted in a temperature range of from −80° C. to a reflux temperature of the solvent, preferably from −40° C. to 20° C., more preferably from −20° C. to 10° C. With respect to the reaction time in this step, the reaction of the base and the 1,4,4$_a$,5,8,9$_a$-hexahydro-1α,4α-methanoanthraquinone derivative (III) is generally conducted for 10 minutes to 2 hours, and the whole reaction is completed in about 10 minutes to 2 hours after the subsequent addition of the allyl derivative (IV).

Incidentally, the 1,4,4$_a$,5,8,9$_a$-hexahydro-4$_a$α-alkenyl-1α,4α-methanoanthraquinone derivative (I) formed can be purified by the conventionally-known method such as recrystallization, column chromatography on silica gel, HPLC or molecular distillation.

STEP 3

This step is a process in which the 1,4,4$_a$,5,8,9$_a$-hexahydro-4$_a$α-alkenyl-1α,4α-methanoanthraquinone derivative (I) obtained in Step 2 is heated in the presence of a dehydrogenating agent or oxidizing agent to conduct a Retro Dieis-Alder reaction and a dehydrogenation reaction at the same time, thereby preparing a naphthoquinone derivative (II). This step can be conducted in accordance with the general procedure for the Retro Dieis-Alder reaction.

More specifically, the 1,4,4$_a$,5,8,9$_a$-hexahydro-4$_a$α-alkenyl-1α,4α-methanoanthraquinone derivative (I) can be heated in the presence of the dehydrogenating agent or oxidizing agent in an inert gas stream to prepare the naphthoquinone derivative (II). In this reaction, the dehydrogenating agent or oxidizing agent is used. Specific examples of the dehydrogenating agent may include 2,3-dichloro-5,6-dicyano-1,4-benzoquinone (DDQ), p-chloranil (tetrachloro-1,4-benzoquinone), o-chloranil (tetrachloro-1,2-benzoquinone) and the like. Specific examples of the oxidizing agent may include oxidizing agents usually used in organic syntheses, such as manganese dioxide, hydrogen peroxide, peracids, chromic anhydride, potassium permanganate, potassium bichromate, nitric acid, ceric ammonium nitrate, air, oxygen, Fremy's salt, ferric chloride and ferric sulfate. No limitation is imposed on the amount of the dehydrogenating agent or oxidizing agent to be used. However, it is generally used in an amount of about 0.5–50 equivalents, preferably about 0.8–20 equivalents, more preferably about 1–10 equivalents based on the 1,4,4$_a$,5,8,9$_a$-hexahydro-4$_a$α-alkenyl-1α,4α-methanoanthraquinone derivative (I). The dehydrogenating agents or oxidizing agents may be used in any combination thereof.

In this reaction, it is preferable to use a solvent. However, no solvent may be used if the 1,4,4$_a$,5,8,9$_a$-methanoanthraquinone hexahydro-4$_a$α-alkenyl-1α, 4α-methanoanthraquinone derivative (I) is liquid or oily. No limitation is imposed on the solvent to be used in this step so long as it is inert on the 1,4,4$_a$,5,8,9$_a$-hexahydro-4$_a$α-alkenyl-1α,4α-methanoanthraquinone derivative (I), dehydrogenating agent or oxidizing agent. Specific examples thereof may include n-butanol, i-butanol, t-butanol, pentyl alcohol, ethylene glycol, propylene glycol, propyl butyrate, butyl butyrate, butyl ether, pentyl ether, cyclohexanone, 2-heptanone, 3-heptanone, 4-heptanone, N,N-dimethylformamide, dimethylsulfoxide, 1,4-dioxane, 1,3-dioxolan, octane, decane, benzene, toluene, xylene, benzyl alcohol, nitrobenzene, etc., with toluene, xylene, ethylene glycol, propylene glycol, propyl butyrate and butyl butyrate being more preferred.

No limitation is imposed on the amount of the solvent to be used. However, it is generally used in an amount of about 0.5–100 parts by volume, preferably about 0.5–50 parts by volume, more preferably about 1–20 parts by volume per part by weight of the 1,4,4$_a$,5,8,9$_a$-hexahydro-4$_a$α-alkenyl -1α,4α-methanoanthraquinone derivative (I). Incidentally, the solvents may be used either singly or in any combination thereof.

The reaction in this step may be conducted in a temperature range of from 60° C. to a reflux temperature of the solvent, preferably from 80° C. to the reflux temperature of the solvent, more preferably from 100° C. to the reflux temperature of the solvent. The reaction is generally completed in about 10 minutes to 2 hours.

The naphthoquinone derivative (II) formed can be purified by the conventionally-known method such as column chromatography on silica gel, HPLC or molecular distillation.

Preparation Examples for providing a starting material required to carry out the present invention will hereinafter be described prior to Examples.

PREPARATION EXAMPLE 1

Synthesis of 5,8-dihydro-2-methyl 1,4-naphthoquinone

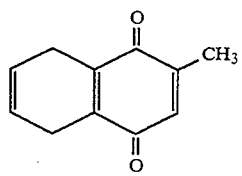

In toluene (30 ml) and acetic acid (5 ml), were dissolved 7.0 g (0,057 mol) of toluquinone, to which 7.6 g (0.14 mol) of 1,3-butadiene were added at −10° C. under stirring. Thereafter, the resultant mixture was gradually heated and stirred further for 3 hours at 40° C. The liquid reaction mixture was washed with water, and an organic layer was dried and concentrated under reduced pressure. Concentrated hydrochloric acid (1 ml) and ethanol (50 ml) were added to the residue, and the mixture was stirred for 1 hour at 40° C. After the liquid reaction mixture was concentrated under reduced pressure, the residue was dissolved in a liquid mixture of toluene (50 ml), n-propanol (25 ml) and water (25 ml). To the solution, were added 1.0 g (0.23 mol) of lithium chloride, 5.0 g (0.29 mol) of cupric chloride dihydrate to stir the resultant mixture for 1 hour at 40° C. The liquid reaction mixture was poured into water (100 ml) to make extraction with toluene (50 ml × 2). The resulting organic layer was washed with water, dried and concentrated under reduced pressure to obtain a crude product of the title compound. This crude product was recrystallized from methanol (20 ml) to obtain 9.14 g of the title compound as yellow crystals (yield: 92%).

Melting point: 91°–92° C. [value in literature: 91°–92° C., Journal of The Chemical Society of Japan, 63(10), 1354–1360 (1942)]

IR (KBr): 1680, 1645 cm$^{-1}$ (C=O).

$^1$H-NMR (90 MHz, CDCl$_3$), δ (ppm): 2.04(3H,d,J=1.4Hz), 3.05(2H,dd,J=1.3Hz), 3.06(2H,dd,J=1.3Hz), 5.8(2H,s), 6.5(1H,dd,J=1.4Hz).

PREPARATION EXAMPLE 2

Synthesis of 5,8-dihydro-1,4-naphthoquinone

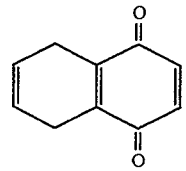

In toluene (30 ml) and acetic acid (10 ml), were dissolved 10.0 g (0.092 mol) of 1,4-benzoquinone, to which 10.0 g (0.18 mol) of 1,3-butadiene were added at −10° C. under stirring. Thereafter, the resultant mixture was gradually heated and stirred further for 3 hours at 40° C. The liquid reaction mixture was washed with water, and an organic layer was dried and concentrated under reduced pressure. Concentrated hydrochloric acid (1 ml) and ethanol (50 ml) were added to the residue, and the mixture was stirred for 1 hour at 40° C. After the liquid reaction mixture was concentrated under reduced pressure, the residue was dissolved in a liquid mixture of acetonitrile (100 ml) and water (30 ml). To the solution, were added 20.0 g (0.036 mol) of ceric ammonium nitrate at room temperature to stir the resultant mixture for 1 hour. The liquid reaction mixture was poured into water (200 ml) to make extraction with toluene (50 ml × 2). The resulting organic layer was washed with water, dried and concentrated under reduced pressure to obtain 13.3 g of a crude product of the title compound (yield: 91%).

This crude product has sufficient purity even if it is not purified.

Melting point: 78°–80° C.

IR (KBr): 1680, 1645 cm$^{-1}$ (C=O).

$^1$H-NMR (90 MHz, CDCl$_3$), δ (ppm): 3.04(2H,dd,J=1.4Hz), 3.06(2H,dd,J=1.4Hz), 5.8(2H,s), 6.5(2H,s).

PREPARATION EXAMPLE 3

Synthesis of 5,8-dihydro-6,7-dimethyl-1,4-naphthoquinone

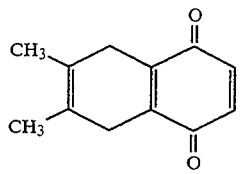

In toluene (60 ml) and acetic acid (10 ml), were dissolved 14.0 g (0.13 mol) of 1,4-benzoquinone, to which 20.0 g (0.24 mol) of 2,3-dimethyl-1,3-butadiene were added at −10° C. under stirring. Thereafter, the resultant mixture was gradually heated and stirred further for 3 hours at 40° C. The liquid reaction mixture was washed with water, and an organic layer was dried and concentrated under reduced pressure. Concentrated hydrochloric acid (1 ml) and ethanol (60 ml) were added to the residue, and the mixture was stirred for 1 hour at 40° C. After the liquid reaction mixture was concentrated under reduced pressure, the residue was dissolved in a liquid mixture of acetonitrile (100 ml) and water (30 ml). To the solution, were added 20.0 g (0.036 mol) of ceric ammonium nitrate at room temperature to stir the resultant mixture for 1 hour. The liquid reaction mixture was poured into water (200 ml) to make extraction with toluene (50 ml × 2). The resulting organic layer was washed with water, dried and concentrated under reduced pressure to obtain 21.5 g of a crude product of the title compound (yield: 88%).

This crude product has sufficient purity even if it is not purified.

Melting point: 84°–85° C.
IR (KBr): 1680, 1645 cm$^{-1}$ (C=0).
$^1$H-NMR (90 MHz, CDCl$_3$), δ (ppm): 1.90(6H,s), 3.05(2H,s), 3.10(2H,s), 6.45(2H,s).

PREPARATION EXAMPLE 4

Synthesis of 5,8-dihydro-2,6,7-trimethyl-1,4-naphthoquinone

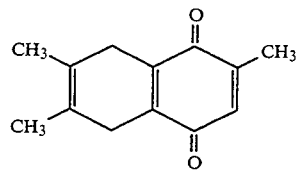

In toluene (30 ml) and acetic acid (10 ml), were dissolved 6.0 g (0.049 mol) of toluquinone, to which 10.0 g (0.12 mol) of 2,3-dimethyl-1,3-butadiene were added at −10° C. under stirring. Thereafter, the resultant mixture was gradually heated and stirred further for 3 hours at 40° C. The liquid reaction mixture was washed with water, and an organic layer was dried and concentrated under reduced pressure. Concentrated hydrochloric acid (1 ml) and ethanol (40 ml) were added to the residue, and the mixture was stirred for 1 hour at 40° C. After the liquid reaction mixture was concentrated under reduced pressure, the residue was dissolved in a liquid mixture of acetonitrile (70 ml) and water (20 ml). To the solution, were added 15.0 g (0.027 mol) of ceric ammonium nitrate at room temperature to stir the resultant mixture for 1 hour. The liquid reaction mixture was poured into water (200 ml) to make extraction with toluene (50 ml × 2). The resulting organic layer was washed with water, dried and concentrated under reduced pressure to obtain 8.9 g of a crude product of the title compound (yield: 91%).

This crude product has sufficient purity even if it is not purified.

Melting point: 87°–89° C.
IR (KBr): 1680, 1645 cm$^{-1}$ (C=0).
$^1$H-NMR (90 MHz, CDCl$_3$), δ (ppm): 1.90(6H,s), 2.05(3H,d,J=1.4Hz), 3.05(2H,s), 3.10(2H,s), 6.50(1H,dd,J=1.4Hz).

The present invention will hereinafter be described specifically by the following Examples. It goes without saying that the present invention is not limited to these examples.

EXAMPLE 1

Synthesis of 1,4,4$_a$,5,8,9$_a$-hexahydro-9$_a$α-methyl-1α,4α-methanoanthraquinone

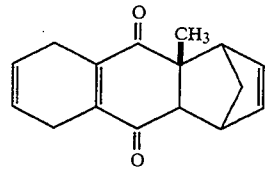

In a liquid mixture of methanol (50 ml) and acetic acid (50 ml), were dissolved 17.4 g (0.1 mol) of 5,8-dihydro-2-methyl-1,4-naphthoquinone, to which 13.2 g (0.2 mol) of fresh cyclopentadiene as distilled were added dropwise over 1 hour at room temperature under stirring. Thereafter, the mixture was stirred for 2 days. The resulting liquid reaction mixture was concentrated under reduced pressure to obtain a pale yellow residue. This residue was recrystallized from methanol (70 ml) to obtain 22.5 g of the title compound as white crystals (yield: 94%).

Melting point: 103°–104° C.
IR (KBr): 1680, 1645 cm$^{-1}$ (C=0).
$^1$H-NMR (90 MHz, CDCl$_3$), δ (ppm): 1.44(3H,s), 1.53(1H,dd,J=1.6Hz), 1.68(1H,dd,J=1.6Hz), 2.82(1H,d,J=3.9Hz), 2.95(2H,dd,J=1.7Hz), 2.97 (2H,dd,J=1.7Hz), 3.08(1H,dd,J=1.7Hz), 3.41(1H,dd,J=1.5Hz), 5.74(2H,dd,J=2.6Hz), 5.94(1H,dd,J=2.4Hz), 6.08 (1H,dd,J=2.4Hz).
MS (FAB): m/z=174 (M-C$_5$H$_6$).

EXAMPLES 2–5

Synthesis of 1,4,4$_a$,5,8,9$_a$-hexahydro-9$_1$α-methyl-1α,4α-methanoanthraquinone 5,8-Dihydro-2-methyl-1,4-naphthoquinone and cyclopentadiene were reacted under the same conditions as those used in Example 1 except that the solvent, acid catalyst and reaction time were changed, thereby obtaining results as shown in the following Table 1.

TABLE 1

| Ex. | Acid catalyst | Solvent | Reaction temperature | Reaction time | Amount formed | Yield |
|---|---|---|---|---|---|---|
| 2 | p-Toluenesulfonic acid 1.0 g | Ethanol 50 | Room temperature | 2 days | 22.3 g | 93% |

TABLE 1-continued

| Ex. | Acid catalyst | Solvent | Reaction temperature | Reaction time | Amount formed | Yield |
|---|---|---|---|---|---|---|
| 3 | Conc. sulfuric acid 0.3 g | ditto ml | ditto | ditto | 21.9 g | 91% |
| 4 | BF$_3$-ether complex 1.0 ml | Tetrahydrofuran 50 ml | ditto | 4 days | 22.1 g | 92% |
| 5 | Tin tetrachloride 1.0 ml | ditto | ditto | ditto | 20.4 g | 85% |

EXAMPLE 6

Synthesis of 1,4,4$_a$,5,8,9$_a$-hexahydro-9$_a$α-methyl-4$_a$α-(3'-methyl-2'-butenyl)-1α,4α-methanoanthraquinone

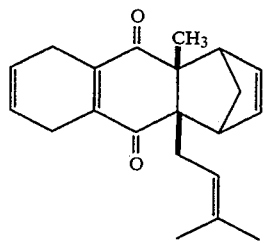

In tetrahydrofuran (100 ml), were dissolved 11.0 g (0.1 mol) of potassium t-butoxide, to which a solution of 12.0 g (0.05 mol) of 1,4,4$_a$,5,8,9$_a$-hexahydro-9$_a$α-methyl-1α,4α-methanoanthraquinone in tetrahydrofuran (60 ml) was added dropwise over 30 minutes at 0°–5° C. in an argon stream. The resultant mixture was stirred for 30 minutes as it is. A solution of 6.2 g (0.05 mol) of 3'-methyl-2'-butenyl bromide (purity: 85%) in tetrahydrofuran (50 ml) was then added dropwise to the liquid reaction mixture over 30 minutes with the liquid reaction mixture kept at 0°–5° C., followed by stirring for additional 1 hour. The resultant liquid reaction mixture was added into 0.1 N hydrochloric acid (200 ml) to make extraction twice with toluene (100 ml × 2). After drying an organic layer, it was concentrated under reduced pressure to obtain a residue in the form of a yellow oil. This residue was purified by column chromatography on silica gel (n-hexane:toluene system), thereby obtaining 13.3 g of the title compound as pale yellow crystals (yield: 86%, HPLC purity: 98.0%).

Melting point: 78°–80° C.

IR (cm$^{-1}$): 1680, 1645 (C=0).

$^1$H-NMR ( 90 MHz, CDCl$_3$), δ (ppm): 1.44(3H,s), 1.46(3H,s), 1.52(1H,dd,J=1.5Hz), 1.55(3H,s), 1.68(1H,dd,J=1.5Hz), 2.47(1H,dd,J=6.5Hz), 2.90(1H,dd,J=6.5Hz), 2.93(2H,dd,J=1.8Hz), 2.96(2H,dd,J=1.8Hz), 3.10(1H,dd,J=1.8Hz), 3.42(1H,dd,J=1.5Hz), 4.88(1H,t,J=6.5Hz), 5-75(2H,dd,J=2–6Hz), 5.93(1H,dd,J=2.5Hz), 6.06(1H,dd,J=2–5Hz).

EXAMPLE 7

Synthesis of 2-methyl-3-(3'-methyl-2'-butenyl)-1,4-naphthoquinone

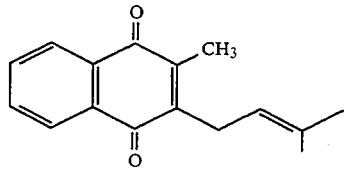

In toluene (30 ml), were dissolved 3.1 g (0.01 mol) of 1,4,4$_a$,5,8,9$_a$-hexahydro-9$_a$α-methyl-4$_a$α-(3'-methyl-2'-butenyl)-1α,4α-methanoanthraquinone and 2.3 g (0.01 mol) of 2,3-dichloro-5,6-dicyano-1,4-benzoquinone (hereinafter abbreviated as DDQ), and the resultant solution was refluxed under heat for 1 hour in an argon stream. The liquid reaction mixture was washed with water, dried and concentrated under reduced pressure to obtain a residue in the form of a yellowish-orange oil. This residue was purified by column chromatography on silica gel (n-hexane:toluene system), thereby obtaining 2.2 g of the title compound as a yellow oil (yield: 92%).

This product was identified with a standard reference material (SRM) in TLC, HPLC and capillary GC.

EXAMPLE 8

Synthesis of 2-methyl-3-(3'-methyl-2'-butenyl)-1,4-naphthoquinone

In toluene (30 ml), were dissolved 3.1 g (0.01 mol) of 1,4,4$_a$,5,8,9$_a$-hexahydro-9$_a$α-methyl-4$_a$α-(3p'-methyl-2'-butenyl)-1α,4α-methanoanthraquinone, and 1.0 g (0.012 mol) of manganese dioxide was suspended in the resulting solution. The suspension was refluxed under heat for 1 hour in an argon stream. The liquid reaction mixture was washed with water, dried and concentrated under reduced pressure to obtain a residue in the form of a yellowish-orange oil. This residue was purified by column chromatography on silica gel (n-hexane:toluene system), thereby obtaining 2.3 g of the title compound as a yellow oil (yield: 96%, HPLC purity: 99.2%).

EXAMPLE 9

Synthesis of 1,4,4$_a$,5,8,9$_a$-hexahydro-9$_a$α-methyl-4$_a$α-[(2'E)-3',7'-dimethyl-2',6'-octadienyl]-1α,4α-methanoanthraquinone

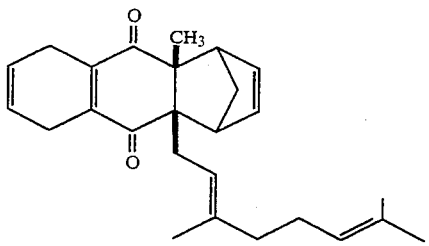

In tetrahydrofuran (50 ml), were dissolved 19.0 g (0.1 mol) of a 28% solution of sodium methoxide in methanol, and the resulting solution, 12.0 g (0.05 mol) of 1,4,4$_a$,5,8,9$_a$-hexahydro-9$_a$α-methyl-1α,4α-methanoanthraquinone and 13.5 g (0.05 mol) of (2E)-geranyl bromide (purity: 80%) were used to conduct a reaction in the same manner as in Example 6, thereby obtaining 16.1 g of the title compound as a yellow oil (yield: 86%, HPLC purity: 98.8%).

IR (cm$^{-1}$): 1675, 1645 (C=O).
$^1$H-NMR (90 MHz, CDCl$_3$), δ (ppm):
1.46(3H,s), 1.48(1H,dd,J=7.1Hz), 1.56(3H,s),
1.57 (3H,s), 1.59(3H,s), 1.82(2H,t,J=4.0Hz),
1.85(2H,t,J=4.0Hz), 1.91(1H,dd,J=7.0Hz),
2.47 (1H,dd,J=7.0Hz), 2.85(1H,dd,J=7.1Hz),
2.95(2H,dd,J=1.8Hz), 2.96(2H,dd,J=1.8Hz),
3.14(1H,s), 3.21(1H,s), 4.8(1H,t,J=6.0Hz),
4.9(1H,t,J=6.0Hz), 5.74(2H,dd,J=2.6Hz),
6.05 (2H, dd,J=3.10Hz).
MS (FAB): m/z=310 (M-C$_5$H$_6$).

EXAMPLE 10

Synthesis of 2-methyl-3-[(2′E)-3′,7′-dimethyl-2′,6′-octadienyl]-1,4-naphthoquinone

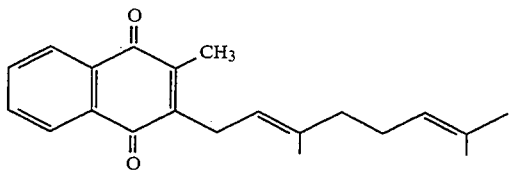

In toluene (30 ml), were dissolved 3.8 g (0.01 mol) of 1,4,4$_a$,5,8,9$_a$-hexahydro-9$_a$α-methyl-4$_a$α-[(2′E)-3′,7′-dimethyl-2′,6′-octadienyl]-1α,4α-methanoanthraquinone and 1.15 g (0.005 mol) of DDQ. The resulting solution was subjected to a reaction and post-treatment in the same manner as in Example 7, thereby obtaining 2.75 g of the title compound as a yellow oil (yield: 89%, HPLC purity: 99%).

This product was identified with a standard reference material (SRM) in TLC, HPLC and capillary GC.

EXAMPLE 11

Synthesis of 2-methyl-3-[(2′E)-3′,7′-dimethyl-2′,6′-octadienyl]-1,4-naphthoquinone In toluene (30 ml), were dissolved 3.3 g (0.0087 mol) of 1,4,4$_a$,5,8,9$_a$-hexahydro-9$_a$α-methyl-4$_a$α-[(2′E)-3′,7′-dimethyl-2′,6′-octadienyl]-1α,4α-methanoanthraquinone, and 0.4 g (0.0046 mol) of manganese dioxide was suspended in the resulting solution to conduct a reaction and post-treatment in the same manner as in Example 7, thereby obtaining 2.5 g of the title compound as a yellow oil (yield: 93% HPLC purity: 99 3%)

EXAMPLE 12

Synthesis of 1,4,4$_a$,5,8,9$_a$-hexahydro-9$_a$α-methyl-4$_a$α-[(2′E,6′E)-3′,7′,11′-trimethyl-2′,6′,10′-dodecatrienyl]-1α,4α-methanoanthraquinone

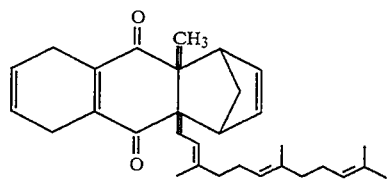

In tetrahydrofuran (100 ml), were dissolved 6.0 g (0.053 mol) of potassium t-butoxide, and the resulting solution, 6.0 g (0.025 mol) of 1,4,4$_a$,5,8,9$_a$-hexahydro-9$_a$α-methyl-1α,4α-methanoanthraquine and 8.9 g (0.025 mol) of (2E,6E)-farnesyl bromide (purity: 80%) were used to conduct a reaction in the same manner as in Example 6, thereby obtaining 10.2 g of the title compound as a yellow oil (yield: 92%, HPLC purity: 98.5%).

IR (cm$^{-1}$): 1675, 1645 (C=O).
$^1$H-NMR (90 MHz, CDCl$_3$), δ (ppm):
1.45(3H,s), 1.47(1H,dd,J=7.0Hz), 1.55(3H,S),
1.57 (6H,s), 1.59(3H,s) , 1.8–1.9(8H,br-d) ,
1.92 (1H,dd,J=7.0Hz), 2.45(1H,dd,J=7.0Hz),
2.8(1H,dd,J=7.0Hz), 2.94(2H,dd,J=1.7Hz),
2.97 (2H,dd,J=1.7Hz), 3.14(1H,s), 3.20(1H,s),
4.7(2H,t,J=6.0Hz), 4.9(1H,t,J=6.0Hz),
5.75(2H,dd,J=2.6Hz), 6.06(2H,dd,J=3.0Hz).
MS (FAB): m/z=378 (M-C$_5$H$_6$).

EXAMPLE 13

Synthesis of 2-methyl-3-[(2′E,6′E)-3′,7′,11′-trimethyl-2′,6′,10′-dodecatrienyl]-1,4-naphthoquinone

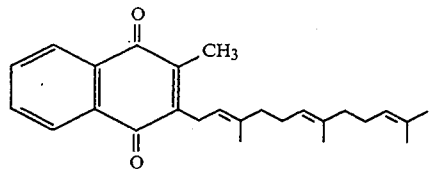

In toluene ( 30 ml ) , were dissolved 4.45 g ( 0.01 tool ) of 1,4,4$_a$,5,8,9$_a$-hexahydro-9$_a$α-methyl-4$_a$α-[(2′E, 6′E)-3′,7′,11′-trimethyl-2′,6′,10′-dodecatrienyl]-1α,4α-methanoanthraquinone and 1.15 g (0.005 mol) of DDQ. The resulting solution was subjected to a reaction and post-treatment in the same manner as in Example 7, thereby obtaining 3.45 g of the title compound as a yellow oil (yield: 92%, HPLC purity: 98.9%).

This product was identified with a standard reference material (SRM) in TLC, HPLC and capillary GC.

EXAMPLE 14

Synthesis of 1,4,4$_a$,5,8,9$_a$-hexahydro-9$_a$α-methyl-4$_a$α-[(2′E,6′E,10′E)-3′,7′,11′,15′-tetramethyl-2′,6′,10′,14′-hexadecatetraenyl]-1α,4α-methanoanthraquinone

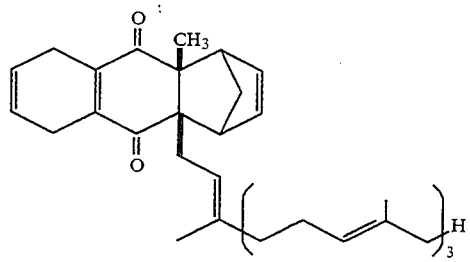

In tetrahydrofuran (200 ml), were dissolved 11.0 g (0.1 mol) of potassium t-butoxide, and the resulting solution, 12.0 g (0.05 mol) of 1,4,4$_a$,5,8,9$_a$-hexahydro9$_a$α-methyl-1α,4α-methanoanthraquine and 22.0 g (0.05 mol) of (2E,6E,10E)-geranylgeranyl bromide (purity: 80%) were used to conduct a reaction in the same manner as in Example 6, thereby obtaining 23.2 g of the title compound as a yellow oil (yield: 91%, HPLC purity: 99.0%) .

IR (cm$^{-1}$): 1675, 1645 (C=O).

¹H-NMR (90 MHz, CDCl₃), δ (ppm):
1.44(3H,s), 1.47(1H,dd,J=6.5Hz), 1.54(3H,s),
1.58(9H,s), 1.60(3H,s), 1.78-1.88(12H,br-d),
1.93(1H,dd,J=6.5Hz), 2.44 ( 1H, dd, J=6.5Hz ),
2.77 (1H,dd,J=6.5Hz), 2.95(2H,dd,J=1.8Hz),
2.98(2H,dd,J=1.8Hz), 3.15(1H,s), 3.20(1H,s),
4.75(3H,t,J=6.0Hz), 4.88(1H,t,J=6.0Hz),
5.75(2H,dd,J=2.5Hz), 6.05 (2H, dd,J=3.0Hz).
MS (FAB): m/z=446 (M-C₅H₆).

EXAMPLE 15

Synthesis of
2-methyl-3-[(2'E,6'E,10'E)-3',7',11',15'-tetramethyl
-2',6',10',14'-hexadecatetraenyl]-1,4-naphthoquinone

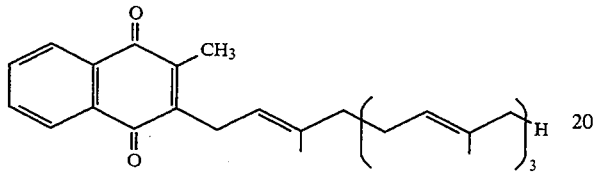

In toluene (30 ml), were dissolved 2.56 g (0.005 mol) of 1,4,4ₐ,5,8,9ₐ-hexahydro-9ₐα-methyl-4ₐα-[(2'E,6'E,1-0'E)-3 ',7',11',15'-tetramethyl-2',6',10',14'-hexadecatetraenyl]-1α,4α-methanoanthraquinone and 0.6 g (0.0025 mol) of DDQ. The resulting solution was subjected to a reaction and post-treatment in the same manner as in Example 7, thereby obtaining 2.05 g of the title compound as a yellow oil (yield: 99%, HPLC purity: 98.9%).

This product was identified with a standard reference material (SRM) in TLC, HPLC and capillary GC.

EXAMPLE 16

Synthesis of
2-methyl-3-[(2'E,6'E,10'E)-3',7',11',15'-tetramethyl-2',6',10',14'-hexadecatetraenyl]-1,4-naphthoquinone In toluene (20 ml), were dissolved 2.56 g (0.005 mol) of 1,4,4ₐ,5,8,9ₐ-hexahydro-9ₐα-methyl-4ₐα-[(2'E,6-'E,10'E) -3',7',11',15'-tetramethyl-2',6',10',14'-hexadecatetraenyl]-1α,4α-methanoanthraquinone, and 0.2 g ( 0. 0023 tool ) of manganese dioxide was suspended in the resulting solution to conduct a reaction and post-treatment in the same manner as in Example 7, thereby obtaining 2.15 g of the title compound as a yellow oil (yield: 97%, HPLC purity: 99.1%).

EXAMPLE 17

Synthesis of
1,4,4ₐ,5,8,9ₐ-hexahydro-9ₐα-methyl-4ₐα-[(2E')-3',7',11',15'-tetramethyl-2'-hexadecaenyl]-1α,4α-methanoanthraquinone

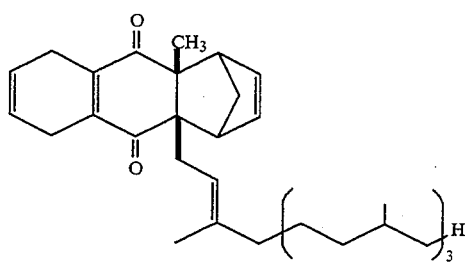

In tetrahydrofuran (100 ml), were dissolved 6.0 g (0.053 mol) of potassium t-butoxide, and the resulting solution, 6.0 g (0.025 mol) of 1,4,4ₐ,5,8,9ₐ-hexahydro-9ₐα-methyl-1α,4α-methanoanthraquinone and 10.8 g (0.025 mol) of (2E)-phytyl bromide (purity: 80%) were used to conduct a reaction in the same manner as in Example 6, thereby obtaining 11.3 g of the title compound as a yellow oil (yield: 87%, HPLC purity: 98.7%).

IR (cm⁻¹): 1675, 1645 (C=0).
¹H-NMR (90 MHz, CDCl₃), δ (ppm):
0.80-0.92 (12H,br-d), 1.0-1.4(16H,m), 1.46(3H,s),
1.49(1H,dd,J=7.0Hz), 1.57 (3H,s), 1.80-1.85(5H,br-d),
1.92(1H,dd,J=7.0Hz), 2.47(1H,dd,J=7.0Hz),
2.85(1H,dd,J=7.0Hz), 2.95(2H,dd,J=1.8Hz),
2.97(2H,dd,J=1.8Hz), 3.13(1H,s), 3.22(1H,s),
4.9(1H,t,J=6.0Hz), 5.75(2H,dd,J=2.5Hz),
6.05 (2H,dd,J=3.6Hz).
MS (FAB): m/z=452 (M-C₅H₆).

EXAMPLE 18

Synthesis of
2-methyl-3-[(2E')-3',7',11',15'-tetramethyl-2'-hexadecaenyl]-1,4 -naphthoquinone

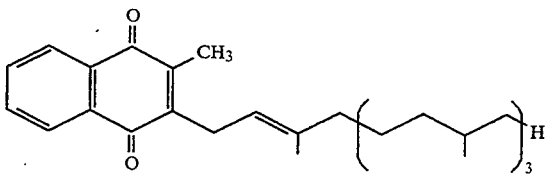

In toluene (20 ml), were dissolved 2.6 g (0.005 mol) of 1,4,4ₐ,5,8,9ₐ-hexahydro-9ₐα-methyl-4ₐα-[(2E')-3',7',11',15'-tetramethyl-2'-hexadecaenyl]-1α,4α-methanoanthraquinone and 0.6 g (0.0025 mol) of DDQ. The resulting solution was subjected to a reaction and post-treatment in the same manner as in Example 7, thereby obtaining 2.04 g of the title compound as a yellow oil (yield: 93%, HPLC purity: 99.3%).

This product was identified with a standard reference material (SRM) in TLC, HPLC and capillary GC.

EXAMPLE 19

Synthesis of
1,4,4ₐ,5,8,9ₐ-hexahydro-1α,4α-methanoanthraquinone

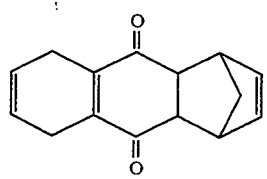

In a liquid mixture of methanol (30 ml) and acetic acid (30 ml), were dissolved 8.3 g (0.051 mol) of 5,8-dihydro-1,4-naphthoquinone, to which 6.6 g (0.1 mol) of fresh cyclopentadiene as distilled were added dropwise over 1 hour at room temperature under stirring. Thereafter, the mixture was stirred for 2 hours. The resulting liquid reaction mixture was concentrated under reduced pressure to obtain a pale yellow residue. This residue was recrystallized from methanol (40 ml) to obtain 2.5 g of the title compound as white crystals (yield: 2%).

Melting point: 114°-115.5° C. (decomposed)
IR (KBr): 1675, 1640 cm⁻¹ (C=0).

$^1$H-NMR (90 MHz, CDCl$_3$), δ (ppm):
1.54(1H,dd,J=1.5Hz), 1.68(1H,dd,J=1.5Hz),
2.70(2H,dd,J=2.7Hz), 3.00(2H,dd,J=1.7Hz),
3.05(2H,dd,J=1.7Hz), 3.10(1H,dd,J=1.8Hz),
3.45(1H,dd,J=1.8Hz), 5.75(2H,dd,J=2.5Hz),
5.95(1H,dd,J=2.4Hz), 6.10 (1H, dd,J=2.4Hz).
MS (FAB): m/z=160 (M-C$_5$H$_6$).

EXAMPLE 20

Synthesis of 1,4,4$_a$,5,8,9$_a$-hexahydro-6,7-dimethyl-1α,4α-methanoanthraquinone

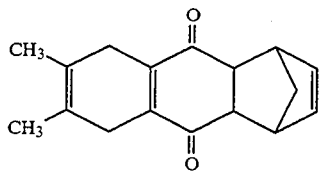

In a liquid mixture of methanol (50 ml) and acetic acid (50 ml), were dissolved 18.8 g (0.1 tool) of 5,8-dihydro-6,7-dimethyl-1,4-naphthoquinone, to which 13.2 g (0.2 mol) of fresh cyclopentadiene as distilled were added dropwise over 1 hour at room temperature under stirring. Thereafter, the mixture was stirred for 2 hours. The resulting liquid reaction mixture was concentrated under reduced pressure to obtain a pale yellow residue. This residue was recrystallized from methanol (70 ml) to obtain 22.1 g of the title compound as white crystals (yield: 91%).

Melting point: 120°-122° C. (decomposed) IR (KBr): 1675, 1640 cm$^{-1}$ (C=O).

$^1$H-NMR (90 MHz, CDCl$_3$), δ (ppm):
1.55(1H,dd,J=1.6Hz), 1.68(1H,dd,J=1.6Hz),
1.90(6H,s), 3.05(2H,s), 3.10(2H,s)
3.38(1H,dd,J=1.8Hz), 3.42(1H,dd,J=1.8Hz),
3.55(1H,dd,J=1.5Hz), 3.62(1H,dd,J=1.5Hz),
5.75 (2H, dd,J=2.5Hz).
MS (FAB): m/z=178 (M-C$_5$H$_6$).

EXAMPLE 21

Synthesis of 1,4,4$_a$,5,9$_a$-hexahydro-6,7,9$_a$α-trimethyl-1α,4α-methanoanthraquinone

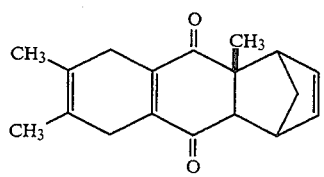

In a liquid mixture of methanol (30 ml) and acetic acid (30 ml), were dissolved 10.1 g (0.05 mol) of 5,8-dihydro-2,6,7-trimethyl-1,4-naphthoquinone, to which 6.6 g (0.1 mol) of fresh cyclopentadiene as distilled were added dropwise over 1 hour at room temperature under stirring. Thereafter, the mixture was stirred for 2 hours. The resulting liquid reaction mixture was concentrated under reduced pressure to obtain a pale yellow residue. This residue was recrystallized from methanol (40 ml) to obtain 11.7 g of the title compound as white crystals (yield: 88%).

Melting point: 96°-97° C. (decomposed)
IR (KBr): 1680, 1645 cm$^{-1}$ (C=O).

$^1$H-NMR (90 MHz, CDCl$_3$), δ (ppm):
1.44(3H,s), 1.54(1H,dd,J=1.6Hz),
1.68(1H,dd,J=1.6Hz), 1.92(6H,s),
2.84(1H,dd,J=3.1Hz), 2.95(2H,s), 3.05(2H,s)
3.08 (1H,dd,J=1.5Hz), 3.40(1H,dd,J=1.5Hz),
5.76 (2H, dd,J=2.5Hz).
MS (FAB): m/z=202 (M-C$_5$H$_6$).

EXAMPLE 22

Synthesis of 1,4,4$_a$,5,8,9$_a$-hexahydro-4$_a$α-[(2'E)-3',7'-dimethyl-2',6'-octadienyl]-1α,4α-methanoanthraquinone

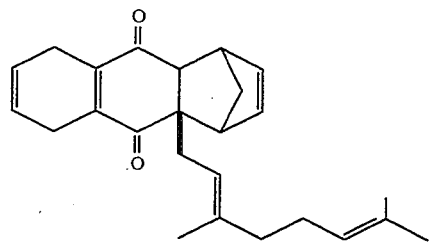

In tetrahydrofuran (100 ml), were dissolved 6.0 g (0.053 mol) of potassium t-butoxide, to which a solution of 4.5 g (0.02 mol) of 1,4,4$_a$,5,8,9$_a$-hexahydro-1α,4α-methanoanthraquinone in tetrahydrofuran (50 ml) was added dropwise over 30 minutes at 0°-5° C. in an argon stream. The resultant mixture was stirred for 30 minutes as it is. A solution of 6.7 g (0.025 mol) of (2E)-geranyl bromide (purity: 80%) in tetrahydrofuran (50 ml) was then added dropwise to the liquid reaction mixture over 30 minutes with the liquid reaction mixture kept at 0°-5° C., followed by stirring for additional 1 hour. The resultant liquid reaction mixture was added into 0.1 N hydrochloric acid (200 ml) to make extraction twice with toluene (100 ml × 2). After drying an organic layer, it was concentrated under reduced pressure to obtain a residue in the form of a pale yellow oil. This residue was purified by column chromatography on silica gel (n-hexane:toluene system), thereby obtaining 6.6 g of the title compound (yield: 91%, HPLC purity: 98.7 %).

IR (cm$^{-1}$): 1675, 1645 (C=O).

$^1$H-NMR (90 MHz, CDCl$_3$), δ (ppm):
1.46(1H,dd,J=7.0Hz), 1.58(3H,s), 1.60(3H,s),
1.62(3H,s), 1.83(2H,t,J=4.0Hz), 1.85(2H,t,J=4.0Hz),
1.91(1H,dd,J=7.0Hz), 2.45(1H,dd,J=7.0Hz),
2.79(1H,dd,J=7.0Hz), 2.94(2H,dd,J=1.8Hz),
2.96(2H,dd,J=1.8Hz), 3.10(1H,dd,J=1.5Hz),
3.18 (2H, dd, J=4.0Hz ), 4.80 (1H, t, J=6.0Hz),
4.92(1H,t,J=6.0Hz), 5.75(2H,dd,J=2.7Hz),
6.07 (2H, dd, J=3.2Hz).
MS (FAB): m/z=286 (M-C$_5$H$_6$).

EXAMPLE 23

Synthesis of 1,4,4$_a$,5,8,9$_a$-hexahydro-9$_a$α-methyl-4$_a$α[(2'E)-3',7'-dimethyl-2',6'-octadienyl)-1α,4α-methanoanthraquinone

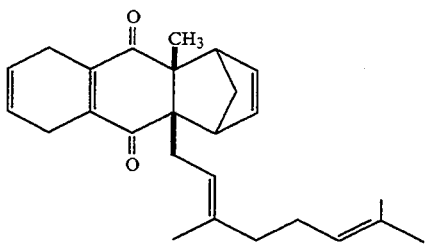

In tetrahydrofuran (100 ml), were dissolved 2.2 g (0.02 mol) of potassium t-butoxide, to which a solution of 3.6 g (0.01 mol) of 1,4,4$_a$,5,8,9$_a$-hexahydro-4$_a$α-[(2'E)-3',7'-dimethyl-2',6'-octadienyl]-1α,4α-methanoanthraquinone in tetrahydrofuran (50 ml) was added dropwise over 30 minutes at 0°–5° C. in an argon stream. The resultant mixture was stirred for 30 minutes as it is. A solution of 1.7 g (0.012 mol) of methyl iodide in tetrahydrofuran (50 ml) was then added dropwise to the liquid reaction mixture over 30 minutes with the liquid reaction mixture kept at 0°–5° C., followed by its stirring further for 1 hour. The resultant liquid reaction mixture was added into 0.1 N hydrochloric acid (200 ml) to make extraction twice with toluene (100 ml × 2). After drying an organic layer, it was concentrated under reduced pressure to obtain a residue in the form of a yellow oil. This residue was purified by column chromatography on silica gel (n-hexane:toluene system), thereby obtaining 3.3 g of the title compound (yield: 89%, HPLC purity: 99.0%).

EXAMPLE 24

Synthesis of 1,4,4$_a$,5,8,9$_a$-hexahydro-4$_a$α-[(2'E,6'E,10'E)-3',7',11',15'-tetramethyl-2',6',10',14'-hexadecatetraenyl)-1α,4α-methanoanthraquinone

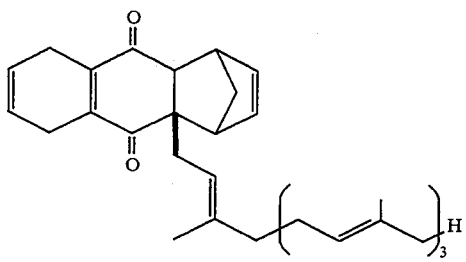

In tetrahydrofuran (100 ml), were dissolved 11.0 g (0.1 mol) of potassium t-butoxide, and the resulting solution, 11.3 g (0.05 mol) of 1,4,4$_a$,5,8,9$_a$-hexahydro-1α,4α-methanoanthraquinone and 22.0 g (0.05 mol) of (2E,6E,10E)-geranylgeranyl bromide (purity: 80%) were used to conduct a reaction in the same manner as in Example 6, thereby obtaining 21.2 g of the title compound as a yellow oil (yield: 85%, HPLC purity: 99.2%).

IR (cm$^{-1}$): 1675, 1645 (C=O).

$^1$H-NMR (90 MHz, CDCl$_3$), δ (ppm):
1.48(1H,dd,J=6.2Hz), 1.53(3H,s), 1.58 (9H, s), 1.62(3H,S), 1.77–1.88(12H,br-d), 1.92(1H,dd,J=6.2Hz), 2.45(1H,dd,J=7.0Hz), 2.78(1H,dd,J=7.0Hz), 2.95(2H,dd,J=1.8Hz), 2.98(2H,dd,J=1.8Hz), 2.98(2H,dd,J=1.8Hz), 3.10(1H,dd,J=1.5Hz), 3.18(2H,dd,J=4.0Hz), 4.80(1H,t,J=6.0Hz), 4.90(1H,t,J=6.0Hz), 5.75(2H,dd,J=2.8Hz), 6.08 (2H, dd ,J=3.2Hz).
MS (FAB): m/z=432 (M-C$_5$H$_6$).

EXAMPLE 25

Synthesis of 2,methyl-3-[(2'E, 6'E, 10'E)-3',7',11',15'-tetramethyl-2',6',10',14'-hexadecatetraenyl]-1,4-naphthoquinone

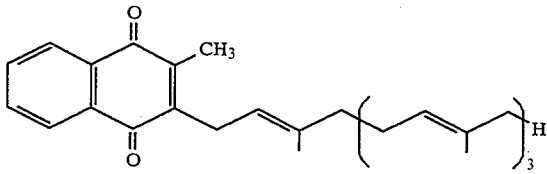

In tetrahydrofuran (80 ml), were dissolved 2.2 g (0.02 mol) of potassium t-butoxide, to which a solution of 5.0 g (0.01 mol) of 1,4,4$_a$,5,8,9$_a$-hexahydro-4$_a$α-(2'E,6'E,10'E) -3',7',11',15'-tetramethyl-2',6',10',14'-hexadecatetraenyl]-1α,4αmethanoanthraquinone tetrahydrofuran (50 ml) was added dropwise over 30 minutes at 0°–5° C. in an argon stream. The resultant mixture was stirred for 30 minutes as it is. A solution of 1.6 g (0.012 mol) of methyl iodide in tetrahydrofuran (50 ml) was then added dropwise to the liquid reaction mixture over 30 minutes with the liquid reaction mixture kept at 0°–5° C., followed by its stirring further for 1 hour. The resultant liquid reaction mixture was added into 0.1 N hydrochloric acid (200 ml) to make extraction twice with toluene (100 ml × 2). After drying an organic layer, it was concentrated under reduced pressure to obtain 4.7 g of a residue in the form of a yellow oil.

This residue was dissolved in toluene (20 ml), and 0.5 g (0.0057 mol) of manganese dioxide was suspended in the resulting solution to conduct a reaction and post-treatment in the same manner as in Example 7, thereby obtaining 3.7 g of the title compound as a yellow oil (yield: 91%, HPLC purity: 99.1%).

EXAMPLE 26

Synthesis of 1,4,4$_a$,5,8,9$_a$-hexahydro-6,7-dimethyl-4$_a$α-[(2'E,6'E)-3',7',11'-trimethyl-2',6',10'-dodecatrienyl)-1α,4α-methanoanthraquinone

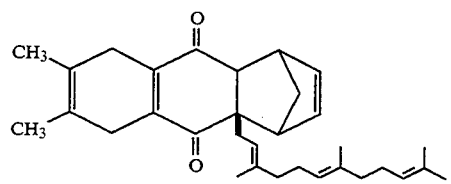

In tetrahydrofuran (100 ml), were dissolved 9.5 g (0.05 mol) of a 28% solution of sodium methoxide in methanol, and the resulting solution, 6.1 g (0,025 mol) of 1,4,4$_a$,5,8,9$_a$-hexahydro-6,7-dimethyl-1α,4α-methanoanthraquinone and 8.9 g (0,025 mol) of (2E)-farnesyl bromide (purity: 80%) were used to conduct a reaction in the same manner as in Example 6, thereby obtaining 9.8 g of the title compound as a yellow oil (yield: 86%, HPLC purity: 98.4%).

IR (cm⁻¹): 1675, 1645 (C=O).
¹H-NMR (90 MHz, CDCl₃), δ (ppm):
1.45(1H,dd,J=7.0Hz), 1.55(3H,s), 1.57 (6H,s),
1.59(3H,s), 1.8–1.9(8H,br-d), 1.92(6H,s),
1.94(1H,dd,J=7.0Hz), 2.45(1H,dd,J=7.0Hz),
2.80(1H,dd,J=7.0Hz), 2.95(2H,dd,J=1.7Hz),
2.98(1H,dd,J=1.7Hz), 3.17 (2H,d,J=7.0Hz),
4.70(2H,t,J=6.0Hz), 4.90(1H,t,J=6.0Hz),
5.75 (2H,dd,J=2.8Hz)
MS (FAB): m/z=392 (M-C₅H₆).

EXAMPLE 27

Synthesis of
1,4,4$_a$,5,8,9$_a$-hexahydro-6,7,9$_a$α-trimethyl-4$_a$α-[(2'E)
-3',7',11',15'-tetramethyl-2'-hexadecaenyl]-1α,4α-
methanoanthraquinone

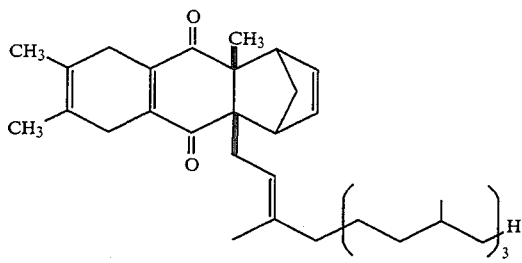

In tetrahydrofuran (100 ml), were dissolved 5.5 g (0.05 mol) of potassium t-butoxide, and the resulting solution, 6.7 g (0,025 mol) of 1,4,4$_a$,5,8,9$_a$-hexahydro-6,7,9$_a$α-trimethyl-1α,4α-methanoanthraquinone and 10.8 g (0,025 tool) of (2E)-phytyl bromide were used to conduct a reaction in the same manner as in Example 6, thereby obtaining 11.1 g of the title compound as a yellow oil (yield: 81%, HPLC purity: 98.8%).

IR (cm⁻¹): 1675, 1645 (C=O).
¹H-NMR (90 MHz, CDCl₃), δ (ppm):
0.8–0.92(12H,br-d), 1.0–1.4(16H,m), 1.47(3H,s),
1.49(1H,dd,J=7.0Hz), 1.57(3H,s), 1.8–1.85(5H,br-d),
1.90(6H,s), 1.93(1H,dd,J=7.0Hz),
2.47 (1H,dd,J=7.0Hz), 2.85(1H,dd,J=7.0Hz),
2.95(2H,dd,J=1.8Hz), 2.98(2H,dd,J=1.8Hz),
3.13(1H,s), 3.22(1H,s), 4.90(1H,t,J=6.0Hz),
5.80 ( 2H, dd ,J=3.6Hz ).
MS (FAB):m/z=480 (M-C₅H₆).

EXAMPLE 28

Synthesis of
2,6,7-trimethyl-3-[(2'E,6'E)-3',7',11'-trimethyl
-2',6',10'-dodecatrienyl]-1,4-naphthoquinone

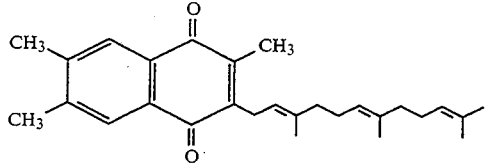

In tetrahydrofuran (80 ml), were dissolved 2.2 g (0.02 mol) of potassium t-butoxide, to which a solution of 4.5 g (0.01 mol) of 1,4,4$_a$,5,8,9$_a$-hexahydro-6,7-dimethyl- 4$_a$α-[(2'E,6'E) -3',7',11'-trimethyl-2',6',10'-dodecatrienyl]-1α,4α-methanoanthraquinone in tetrahydrofuran (50 ml) was added dropwise over 30 minutes at 0°–5° C. in an argon stream. The resultant mixture was stirred for 30 minutes as it is. A solution of 1.6 g (0.012 mol) of methyl iodide in tetrahydrofuran (50 ml) was then added dropwise to the liquid reaction mixture over 30 minutes with the liquid reaction mixture kept at 0°–5° C., followed by its stirring further for 1 hour. The resultant liquid reaction mixture was added into 0.1 N hydrochloric acid (200 ml) to make extraction twice with toluene (100 ml × 2). After drying an organic layer, it was concentrated under reduced pressure to obtain 4.4 g of a residue in the form of a yellow oil.

This residue was dissolved in toluene (20 ml), and 0.5 g (0.0057 mol) of manganese dioxide was suspended in this solution to conduct a reaction and post-treatment in the same manner as in Example 7, thereby obtaining 3.6 g of the title compound as a yellow oil (yield: 89%, HPLC purity: 99.0%).

IR (cm⁻¹): 1680, 1645 (C=O).
¹H-NMR (90 MHz, CDCl₃), δ (ppm):
1.56(3H,s), 1.58(3H,s), 1.60(3H,s),
1.8–1.92(8H,br-d), 2.10(3H,s), 2.20(6H,s),
3.20(2H,d,J=7.0Hz), 4.70(2H,t,J=6.0Hz),
4.90(1H,t,J=6.0Hz), 7.70(2H,s).
MS (FAB): m/z=404.

EXAMPLE 29

Synthesis of
2,6,7-trimethyl-3-[(2'E)-3',7',11',15'-tetramethyl-2'-hexadecaenyl]-1,4-naphthoquinone

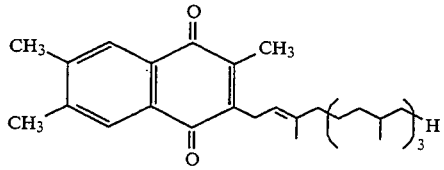

In tetrahydrofuran (80 ml), were dissolved 2.2 g (0.02 mol) of potassium t-butoxide, to which a solution of 5.5 g (0.01 mol) of 1,4,4$_a$,5,8,9$_a$-hexahydro-6,7,9$_a$α-trimethyl-4$_a$α-[(2'E)-3'-,7',11',15'-tetramethyl-2'-hexadecaenyl]--1α,4α-methanoanthraquinone in tetrahydrofuran (50 ml) was added dropwise over 30 minutes at 0°–5° C. in an argon stream. The resultant mixture was stirred for 30 minutes as it is. A solution of 1.6 g (0.012 mol) of methyl iodide in tetrahydrofuran (50 ml) was then added dropwise to the liquid reaction mixture over 30 minutes with the liquid reaction mixture kept at 0°–5° C., followed by its stirring further for 1 hour. The resultant liquid reaction mixture was added into 0.1 N hydrochloric acid (200 ml) to make extraction twice with toluene (100 ml × 2). After drying an organic layer, it was concentrated under reduced pressure to obtain a residue in the form of a yellow oil.

This residue was dissolved in toluene (20 ml), and 0.6 g (0.0069 mol) of manganese dioxide was suspended in this solution to conduct a reaction and post-treatment in the same manner as in Example 7, thereby obtaining 4.5 g of the title compound as a yellow oil (yield: 94%, HPLC purity: 99.2%).

IR (cm⁻¹): 1680, 1645 (C=O).
¹H-NMR (90 MHz, CDCl₃), δ (ppm):
0.8–0.93(12H,br-d), 1.0–1.4(16H,m), 1.57(3H,s),
1.8–1.85(5H,br-d), 2.10(3H,s), 2.28(6H,s), 3.15(2H,d,J=6.0Hz), 4.90(1H,t,J=6.0Hz), 7.70(2H,s).
MS (FAB): m/z=478.

What is claimed is:

1. A process for the preparation of a naphthoquinone derivative represented by the following formula (II):

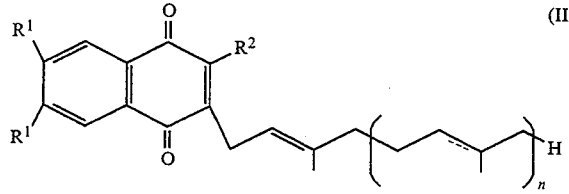
(II)

wherein $R^1$ means a hydrogen atom or methyl group, $R^2$ is a hydrogen atom or methyl group, n stands for 0 or an integer of 1–9, and a linkage ⚌ is a single bond or double bond with the proviso that if n is an integer of 2–9, the linkages may be identical with or different optionally from each other, which comprises subjecting a 1,4,4$_a$,5,8,9$_a$-hexahydro-4$_a$α-alkenyl-1α,4α-methanoanthraquinone derivative represented by the following formula (I):

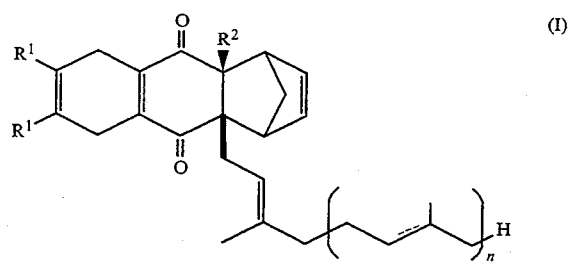
(I)

wherein $R^1$, $R^2$, n and a linkage ⚌ have the same meaning as defined above, to a Retro Dieis-Alder reaction in the presence of a dehydrogenating agent or oxidizing agent.

2. A process for the preparation of a naphthoquinone derivative represented by the following formula (II):

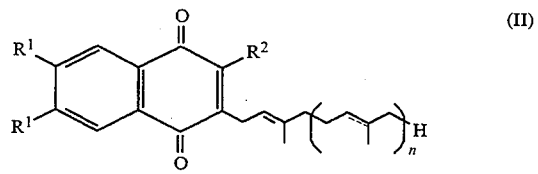
(II)

wherein $R^1$ means a hydrogen atom or methyl group, $R^2$ is a hydrogen atom or methyl group, n stands for 0 or an integer of 1–9, and a linkage ⚌ is a single bond or double bond with the proviso that if n is an integer of 2–9, the linkages may be identical with or different from each other, which comprises reacting a 1,4,4$_a$,5,8,9$_a$-hexahydro-1α,4α-methanoanthraquinone derivative represented by the following formula (III):

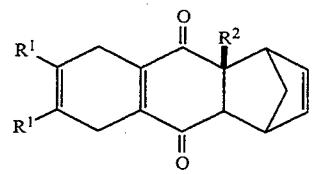
(III)

wherein $R^1$ and $R^2$ have the same meaning as defined above, with an allyl derivative represented by the following formula (IV):

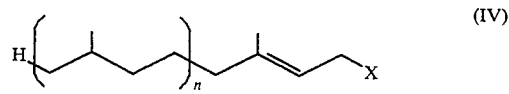
(IV)

wherein n and a linkage ⚌ have the same meaning as defined above, and X means a halogen atom, alkylsulfonyl group or arylsulfonyl group, in the presence of a base to form a 1,4,4$_a$,5,8,9$_a$-hexahydro-4$_a$α-alkenyl-1α,4α-methanoanthraquinone derivative represented by the following formula (I):

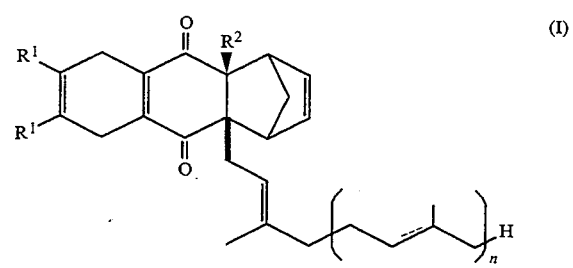
(I)

wherein $R^1$, $R^2$, n and a linkage ⚌ have the same meaning as defined above, and then subjecting the thus-formed derivative (I) to a Retro Dieis-Alder reaction in the presence of a dehydrogenating agent or oxidizing agent.

3. A process for the preparation of a naphthoquinone derivative represented by the following formula (II):

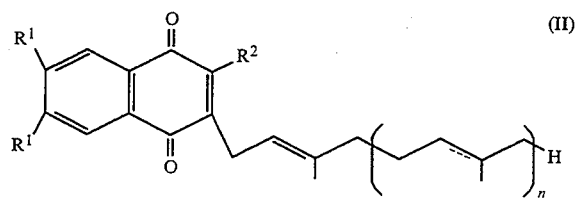
(II)

wherein $R^1$ means a hydrogen atom or methyl group, $R^2$ is a hydrogen atom or methyl group, n stands for 0 or an integer of 1–9, and a linkage ⚌ is a single bond or double bond with the proviso that if n is an integer of 2–9, the linkages may be identical with or different optionally from each other, which comprises subjecting a 5,8-dihydro-1,4-naphthoquinone derivative represented by the following formula (V):

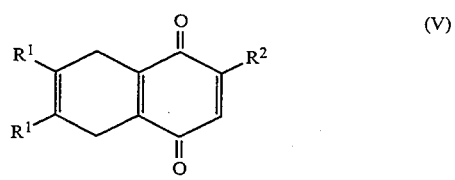
(V)

wherein $R^1$ and $R^2$ have the same meaning as defined above, and cyclopentadiene to a Dieis-Alder reaction to form a 1,4,4$_a$,5,8,9$_a$-hexahydro-1α,4α-methanoanthraquinone derivative represented by the following formula (III):

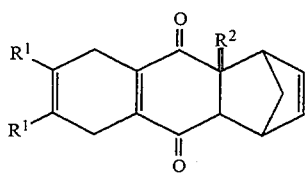

wherein $R^1$ and $R^2$ have the same meaning as defined above, followed by reacting the derivative (III) with an allyl derivative represented by the following formula (IV):

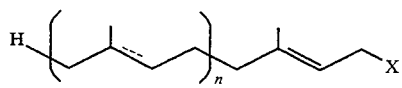

wherein n, and a linkage ⎯ have the same meaning as defined above, and X means a halogen atom, alkylsulfonyl group or arylsulfonyl group in the presence of a base to form a 1,4,4$_a$,5,8,9$_a$-hexahydro-4$_a$α-alkenyl-1α,-4α-methanoanthraquinone derivative represented by the following formula (I):

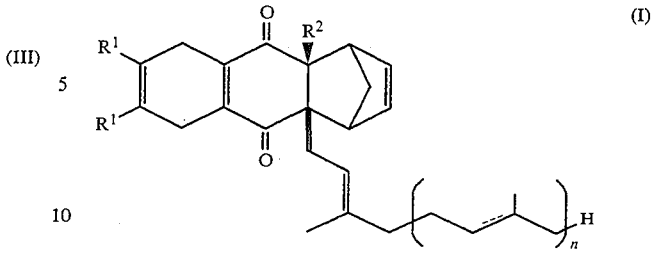

wherein $R^1$, $R^2$, n and a linkage ⎯ have the same meaning as defined above, and subjecting the thus-formed derivative (I) to a Retro Dieis-Alder reaction in the presence of a dehydrogenating agent or oxidizing agent.

4. The process as claimed in claim 3, wherein the 5,8-dihydro-1,4-naphthoquinone derivative (V) is one selected from 5,8-dihydro-1,4-naphthoquinone, 5,8-dihydro-2-methyl-1,4-naphthoquinone, 5,8-dihydro-6,7-dimethyl-1,4-naphthoquinone and 5,8-dihydro-2,6,7-trimethyl-1,4-naphthoquinone.

5. The process as claimed in any one of claims 2 to 3, wherein the base is at least one selected from sodium methoxide, sodium ethoxide, potassium methoxide, potassium ethoxide, potassium t-butoxide, sodium hydride, potassium hydride, calcium hydride, n-butyllithium, metal amides, lithium dialkylamides, sodium hydroxide, potassium hydroxide, sodium carbonate and potassium carbonate.

6. The process as claimed in any one of claims 1 to 3, wherein the dehydrogenating agent is at least one selected from 2,3-dichloro-5,6-dicyano-1,4-benzoquinone, p-chloranil and o-chloranil.

7. The process as claimed in any one of claims 1 to 3, wherein the oxidizing agent is manganese dioxide.

* * * * *